United States Patent [19]

Ballschuh et al.

[11] Patent Number: 5,099,043
[45] Date of Patent: Mar. 24, 1992

[54] 3-METHYLSULFONYLMETHYL-4-SULFOMETHYL-PYRROLIDINIUM-BETAINES AND PROCESS FOR THEIR PREPARATION

[76] Inventors: Detlef Ballschuh; Roland Ohme; Horst Seibt; Egon Gründemann, all of Institut für chemische Technologie Patentbüro Rudower Chaussee 5, 0-1199 Berlin, Fed. Rep. of Germany

[21] Appl. No.: 629,379

[22] Filed: Dec. 18, 1990

[30] Foreign Application Priority Data

Dec. 21, 1989 [DD] German Democratic Rep. ..................................... 3360931

[51] Int. Cl.$^5$ ............................................. C07D 207/08
[52] U.S. Cl. ....................................... 548/570; 548/568
[58] Field of Search .............................. 548/570, 568

[56] References Cited

U.S. PATENT DOCUMENTS

| | | | |
|---|---|---|---|
| 4,410,709 | 10/1983 | Ohme et al. ............... | 548/570 |
| 4,528,383 | 7/1985 | Schmitt ..................... | 548/570 X |
| 4,877,885 | 10/1989 | Ballschuh et al. ......... | 548/570 |

*Primary Examiner*—Joseph Paul Brust

[57] ABSTRACT

The invention relates to novel 3-methylsulfonylmethyl-4-sulfomethyl-pyrrolidinium betaines (methylsulfonyl-sulfobetaines) of the general formula I, which can be used as intermediates for further syntheses or, if they contain a long-chain alkyl radical, as polyfunctional surfactants or hydrotopes [sic]. Molar quantities of a diallylammonium salt are reacted together with chloroacetic acid and twice the molar quantity of sodium hydrogen sulfite in the presence of a catalytic quantity of a peroxodisulfate and the reaction solution obtained is, after addition of a catalytic quantity of iodide as well as calcium carbonate, converted to 3-methylsulfonylmethyl-4-sulfomethyl-pyrrolidinium betaines I by heating until the evolution of carbon dioxide has ceased.

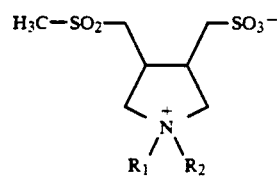

13 Claims, No Drawings

3-METHYLSULFONYLMETHYL-4-SULFOMETHYL-PYRROLIDINIUM-BETAINES AND PROCESS FOR THEIR PREPARATION

The invention relates to novel 3-methylsulfonylmethyl-4-sulfomethyl-pyrrolidinium betaines (methylsulfonylsulfobetaines) of the general formula I

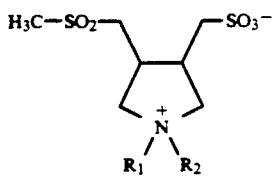

in which $R_1$ and $R_2$ are hydrogen, a straight-chain or branched alkyl radical having 1 to 22 carbon atoms or an alkyl radical which can contain the group —$CH_2$—CONH— at the start of the chain.

As organic intermediates of sulfobetaine character, the novel methylsulfonyl-sulfobetaines of the formula I represent a component for further syntheses. If at least one of the substituents $R_1$ to $R_2$ is a long-chain alkyl radical, these compounds can be used as polyfunctional surfactants, short-chain representatives can furthermore, find use as hydotopes [sic].

Methylsulfonyl-sulfobetaines of the formula I and processes for the preparation thereof have not hitherto been disclosed. Other dialkyl sulfones have been known for a long time [K. Schank in "Methoden der organischen Chemie [Methods of Organic Chemistry]", Houben-Weyl Volume E11, pages 1145 et seq. (1985) and A. Schöberl and A. Wagner, ibid. Volume IX, page 232 (1955)]. Such sulfones are in general prepared by reacting sodium alkylsulfinates with alkyl halides. In the case of the purely aliphatic sulfones [P. Allen et al., J. org. Chem. 16, 767 (1951)], however, the yields after heating the components in propanol for 28 hours are no higher than 27 to 42%.

Very recently, novel sulfobetaine-substituted sulfinic acids and salts thereof as potential starting materials for the synthesis of novel methylsulfonyl-sulfobetaines have become available as compounds which are easily accessible industrially. Such sulfobetaine-sulfinates are obtained by free radical-initiated sulfocyclosulfination of diallylammonium salts with hydrogen sulfite according to DD 225,128 A1 and EP 163,319 A3.

However, attempts carried out in accordance with the state of the art, for example with sodium 1,1-dimethyl-3-sulfinatomethyl-4-sulfomethyl-pyrrolidinium betaine (sulfobetaine-sulfinate) in water/alcohol, gave only unsatisfactory yields of target products even after long reaction times.

Another method for the preparation of methyl aryl sulfones is described by A. Courtin, H.-R. von Tobel and G. Auerbach, Helv. Chim. Acta 63, 1412 (1980). Accordingly, methyl 2-nitrophenyl sulfone is obtained in 91% yield by heating 1 mol of 2-nitrobenzenesulfinic acid, 2 mol of bromoacetic acid and 2 mol of sodium hydroxide solution for 24 hours, with evolution of carbon dioxide. When chloroacetic acid is used in place of bromoacetic acid, the achievable yield falls to 61.5%.

However, the application of this synthesis method to the abovementioned sulfobetaine-sulfinate also gave reaction solutions which was [sic] composed of a complex mixture of starting products and secondary products, from which it was not possible to separate the target product because of the polar character of the starting products and end products. Furthermore, neither have processes been disclosed for the direct preparation of methyl sulfonyls from the starting products of sulfobetainesulfinates, i.e. diallylammonium salts.

The invention relates to a simple synthesis process for the preparation of 3-methylsulfonylmethyl-4-sulfomethylpyrrolidinium betaines from readily accessible, industrially available starting materials, such as a diallylammonium salt, hydrogen sulfites and halogenoacetic acids, which allows the process steps to be carried out without formation of by-products, with a simultaneously high purity and yield of the target product.

According to the invention, diallylammonium salts, preferably diallylammonium chlorides of the general formula II

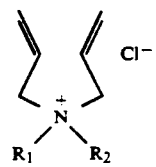

in which $R_1$ and $R_2$ are as defined above, are reacted together with molar quantities of a halogenoacetic acid, preferably chloroacetic acid, and twice the molar quantity of a metal hydrogen sulfite, preferably sodium hydrogen sulfite, in the presence of a catalytic quantity of a peroxodisulfate, and the reaction solution obtained is, after addition of a catalytic quantity of an iodide as well as calcium carbonate, heated to the boil until the evolution of carbon dioxide has ceased. The overall reaction, i.e. the free radical-initiated sulfocyclosulfination of the diallylammonium salt coupled with carboxymethylation/decarboxylation of the sulfobetainesulfinate formed in situ, is illustrated by the following equations:

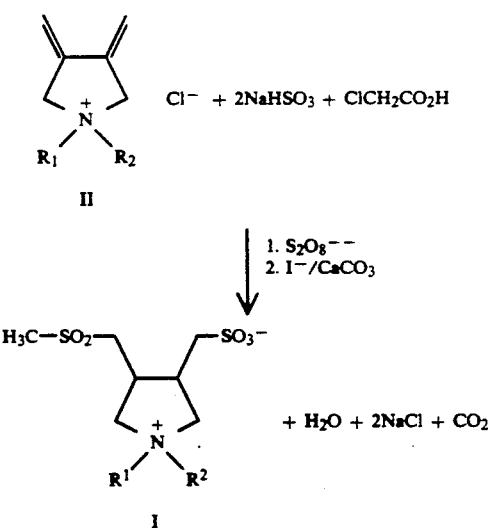

According to DD 225,128 A1, the sulfocyclosulfination of a diallylammonium salt proceeds with maximum yield of the sulfocyclosulfination product (sulfobetainesulfinate) only if pH conditions of around 2 are maintained. Adjustment to this pH is achieved by addition of a mineral acid to the mixture of diallylammonium salt and hydrogen sulfite. Corresponding pH adjustments have hitherto not been carried out with a halogenoacetic acid. It can therefore be regarded as a surprising finding that, for example, the addition of 1 mol of chloroacetic acid to a mixture of 1 mol of diallylammonium salt and 2 mol of technical sodium hydrogen sulfite solution gives the optimum starting pH of around 2, i.e. conditions corresponding to the goal stated above. The order of the combination of the reactants is of no importance for the course of the reaction.

Depending on the quality of the sodium hydrogen sulfite solution used, slight pH fluctuations can occur. They can be corrected either by adding a small quantity of a mineral acid or by starting the reaction with a portion of the halogenoacetic acid and adding the residual quantity of the halogenoacetic acid only during the reaction.

When, for example, tertiary diallylamines are used as the starting products of the reaction, these should preferably be dissolved in the halogenocarboxylic acid and, after addition of the hydrogen sulfite solution, the starting pH should be adjusted with a mineral acid. Since, in the case of tertiary diallylamines and a starting pH of 2.5, the sulfocyclosulfination already proceeds to completion, less than the molar equivalent quantity of mineral acid is required for forming the diallylammonium salt.

For carrying out the first process step, 1 to 5 mol-% of peroxodisulfate, relative to the diallylammonium salt employed, is added to the starting solution which has been prepared in this way and should have a temperature of between 20° and 30° C., in order to initiate the sulfocyclosulfination reaction.

In this case, it has proved to be preferable to add the peroxodisulfate in two portions in order to obtain the most complete conversion possible, quantities of 2 times 2 mol-%, relative to the diallylammonium salt employed, being fully sufficient in most cases. Sodium, potassium or ammonium peroxodisulfate are suitable as peroxodisulfates, which can be employed either as a solution or in powder form. After the addition of peroxodisulfate, the initially pale yellow starting solution assumes a red to blood-red color, but it brightens considerably shortly after passing through the temperature maximum.

To initiate the second synthesis stage, calcium carbonate for neutralizing the acidic reaction solution and a catalytic quantity of a soluble iodide, for example sodium iodide, potassium iodide or ammonium iodide or, if appropriate, iodoacetic acid, are added. With an added quantity of 5 to 13 mmol of sodium iodide, potassium iodide or ammonium iodide/mol of diallylammonium salt, preferably 7 mmol of sodium iodide, potassium iodide or ammonium iodide/mol of diallylammonium salt, complete conversions are achieved in the course of 1 to 2 hours. Whereas quantities of less than 3 mmol of the abovementioned iodides no longer display any catalytic action, quantities greater than 7 mmol further accelerate the reaction, but the crystalline target products will suffer later discoloration.

The mixture is heated further with evaporative cooling until the calcium salt, forming as intermediate, of the carboxy-methylsulfonyl-sulfobetaine has decomposed with decarboxylation and re-formation of calcium carbonate to give the methylsulfonyl-sulfobetaine according to formula I. The end point of the reaction is easily detectable by the precipitation of the calcium carbonate from the reaction solution or by the cessation of carbon dioxide evolution (bubble counter).

Apart from calcium carbonate, other metal carbonates, such as barium carbonate or zinc carbonate, can also be used for neutralizing the above reaction solution, but these have no advantages over calcium carbonate. Moreover, the hydroxides or carbonates of the alkali metals or of ammonia can also be used in place of calcium carbonate for the neutralization; the disadvantage is, however, that the dissolved carbonates then forming can be separated from the target product only with difficulty and, on the other hand, the end point of the reaction is also difficult to detect. By contrast, calcium carbonate can be separated easily by filtration from the reaction solution and can be used again for further batches.

If the carboxymethylation of the sulfocyclosulfination product is carried out without addition of iodide, the desired reaction admittedly takes place in the initial phase, but it slows down with increasing reaction time to such an extent that complete conversion is not achievable even after a long reaction time. The consequence is that the target product can, because of the polar character, not be separated from starting product, intermediate and end product.

Especially pure, i.e. electrolyte-free methylsulfonyl-sulfobetaines are obtained, according to a further embodiment of the process according to the invention, if initially the sulfocyclosulfination product of the diallylammonium salt is reacted with chloroacetic acid in the presence of iodide to give the intermediate, i.e. carboxy-methylsulfonyl-sulfobetaine, and the latter is, after isolation and, if desired, additional recrystallization, decarboxylated with calcium carbonate to give the methylsulfonyl-sulfobetaine according to formula I.

In a further embodiment of the process, previously isolated sulfobetaine-sulfinic acids can also be reacted with chloroacetic acid, catalytic quantities of iodide and calcium carbonate to give the target compounds. However, this synthesis route does not give a process advantage in principle, since the starting sulfobetainesulfinic acids required for this purpose must be prepared beforehand from the corresponding diallylammonium salts.

In summary, the advantage of the invention is a simple synthesis which makes the hitherto unknown 3-methylsulfonylmethyl-4-sulfomethyl-pyrrolidinium betaines of the general formula I accessible directly from diallylammonium salts, without isolation of intermediates. The starting materials used are intermediates which are available on an industrial scale and which can be caused to react in short reaction times by simple means.

The invention will be explained in more detail by the examples which follow.

EXAMPLES

Example 1

1,1-Dimethyl-3-methylsulfonylmethyl-4-sulfomethyl-pyrrolidinium betaine ($R_1=R_2=CH_3$ in the general formula I)

a) 269.5 g (1 mol) of 60% aqueous dimethyldiallylammonium chloride solution, 118.1 g (1 mol) of 80% aqueous chloroacetic acid and 539 g (2.02 mol) of 39% technical sodium hydrogen sulfite solution are introduced into a 1.5 l sulfonation flask, which is fitted with a stirrer, thermometer, reflux condenser and a heat source, and mixed with one another. This gives a pale yellow, homogeneous solution at 21° C. and a starting pH of 2.02. (Fluctuations of the pH, i.e. deviations from the optimum pH of 2, in different batches depend mainly on the quality of the technical sodium hydrogen sulfite solution used and can be corrected either by addition of small quantities of a mineral acid or by omission of a part of the chloroacetic acid, which is then added only after the reaction has taken place). To initiate the reaction, first 4.76 g (2 mol-%) of sodium peroxodisulfate and one minute later—in the meantime, the reaction solution has assumed a blood-red color and the temperature has risen to 60° C.—a further 2 mol-% of sodium peroxodisulfate are added. The reaction temperature maximum of 76° C. is already reached after one further minute. 1.05 g (7 mmol) of sodium iodide and 50 g (0.5 mol) of calcium carbonate are added to the reaction solution. After the main quantity of the calcium carbonate has dissolved with evolution of carbon dioxide, a bubble counter is placed upon the reflux condenser, and the mixture is heated to the boil at 110° C. for 10 to 12 hours until the evolution of carbon dioxide has virtually ceased. (However, the addition of calcium carbonate can also be initially omitted and, instead, the reaction solution can be heated to the boil for 90 minutes and the intermediate, i.e. 1,1-dimethyl-3-carboxymethylsulfonylmethyl-4-sulfomethyl-pyrrolidinium betaine, can be isolated as the crystalline dihydrate from the cooled solution, and this can be reacted with calcium carbonate only afterwards - cf. Example 1b).

The mixture is allowed to cool slightly, the calcium carbonate is filtered off and the filtrate is stored overnight in a refrigerator for crystallization. For working up, the crystal mass is filtered off sharply from the mother liquor with suction, the crystals are rinsed with a little water and twice with alcohol and, after drying in air, a colorless crystal powder is obtained which, for fine purification, can also be recrystallized from water (melting point: starting at 270° C. with decomposition). After the combined mother liquor and rinsing liquor have been further concentrated and left to stand, a further crystalline fraction of the target product can be obtained.

$^{13}$C-NMR spectrum (D$_2$O, external standard tetramethylsilane; TMS; δ=0.0 ppm): the numerical data next to the atom symbols correspond to the chemical shifts for the cis-configuration (3,4-position) in ppm.

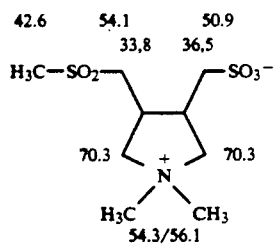

The N—CH$_3$ groups are not equivalent and, as in the case of the N—CH$_2$ groups, there is also an additional signal splitting due to the $^{14}$[lacuna] quadrupole moment.

b) 36.54 g (0.1 mol) of 1,1-dimethyl-3-carboxymethylsulfonylmethyl-4-sulfomethyl-pyrrolidinium betaine dihydrate (the intermediate prepared according to Example 1a and isolated and recrystallized from water; melting point: starting at 290° C. with decomposition), 5 g (0.05 mol) of calcium carbonate and 60 g of water are heated to the boil for 8 hours with evolution of carbon dioxide and separated off from the calcium carbonate which has precipitated. The methylsulfonyl-sulfobetaine crystallizes as the pure compound in virtually quantitative yield from the slightly concentrated filtrate. The $^{13}$C-NMR spectrum is identical to that of the product prepared according to Example 1a.

c) 30.7 g (0.1 mol) of 1,1-dimethyl-3-sulfinato methyl-4-sulfomethyl-pyrrolidinium betaine dihydrate (prepared from dimethyl-diallylammonium chloride and sodium hydrogen sulfite; cf. DD 225,128, Example 13), 11.8 g (0.1 mol) of 80% aqueous chloroacetic acid, 10 g (0.1 mol) of calcium carbonate, 0.15 g (1 mmol) of sodium iodide and 50 g of water are mixed with one another and heated to the boil until the evolution of carbon dioxide ceases (8 hours). The calcium carbonate which has precipitated is filtered off, and working up is carried out according to Example 1a. This gives a crystalline product which is identical to those prepared according to Examples 1a and 1b.

Example 2

1-Dodecyl-1-methyl-3-methylsulfonylmethyl-4-sulfomethylpyrrolidinium betaine (R$_1$=CH$_3$; R$_2$=C$_{12}$H$_{25}$ in the general formula I)

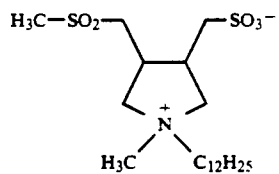

The procedure followed is as in Example 1a, and a mixture at pH 2 of 36 g (0.1 mol) of dodecyl-methyl-diallylammonium bromide, 11.8 g (0.1 mol) of 80% aqueous chloroacetic acid, 53.9 g (0.202 mol) of 39% technical sodium hydrogen sulfite solution is reacted with two portions each of 0.46 g (2 mol-%) of ammonium peroxodisulfate.

5 g (0.05 mol) of calcium carbonate and 0.15 g (1 mmol) of sodium iodide are added to the reaction solution and the latter is heated to the boil until the evolution of carbon dioxide ceases. For the isolation of the pure methylsulfonyl-sulfobetaine, the reaction solution obtained can be further concentrated and extracted with ethanol. When a sample of the reaction product is diluted with water, a vigorously foaming surfactant solution is obtained.

We claim:

1. A 3-methylsulfonylmethyl-4-sulfomethyl-pyrrolidinium betaine of the formula I

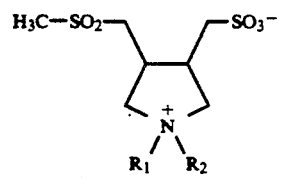

in which

R$_1$ and R$_2$ are hydrogen, a straight-chain or branched alkyl radical having 1 to 22 carbon atoms or a radical —CH$_2$—CONH—alkyl.

2. A compound as claimed in claim 1, wherein $R_1$ and $R_2$ are —$CH_3$.

3. A compound as claimed in claim 1, wherein $R_1$ is —$CH_3$ and $R_2$ is —$C_{12}H_{25}$.

4. A process for the preparation of 3-methylsulfonylmethyl-4-sulfomethylpyrrolidinium betaine of the formula I as claimed in claim 1, which comprises reacting together in solution a diallylammonium salt, with a molar quantity of a monohalogenoacetic acid, and twice the molar quantity of a hydrogen sulfite, in the presence of a catalytic quantity of a peroxodisulfate, and heating the reaction solution obtained, after addition of a catalytic quantity of an iodide as well as calcium carbonate, to the boil until the evolution of carbon dioxide has ceased.

5. The process as claimed in claim 4, wherein 1 to 5 mol-% of peroxodisulfate, relative to the diallylammonium salt employed, is added as the catalyst.

6. The process as claimed in claim 5, wherein the peroxodisulfate is added in two portions each of 2 mol-%, relative to the diallylammonium salt employed.

7. The process as claimed in claim 4, wherein 5 to 13 mmol of sodium, potassium or ammonium iodide/mol of diallylammonium salt are added as the catalytic quantity of iodide.

8. The process as claimed in claim 7, wherein 7 mmol of sodium, potassium or ammonium iodide/mol of diallylammonium salt are added as the catalytic quantity of iodide.

9. The process as claimed in claim 4 wherein the diallylammonium salt is a diallylammonium chloride of the formula II

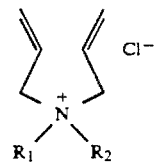

in which
$R_1$ and $R_2$ are hydrogen, a straight-chain or branched alkyl radical having 1 to 22 carbon atoms or a radical —$CH_2$—$CONH$—alkyl.

10. The process as claimed in claim 4, wherein the monohalogenoacetic acid is chloroacetic acid.

11. The process as claimed in claim 4, wherein said hydrogen sulfite is sodium hydrogen sulfite.

12. The process as claimed in claim 4, wherein the peroxodisulfate is added in two portions each of 2 mol-%, relative to the diallylammonium salt employed.

13. The process as claimed in claim 4, wherein 7 mmole of sodium, potassium, or ammonium iodide/mole of diallylammonium salt are added as the catalyst in the second process step.

* * * * *